(12) United States Patent
German et al.

(10) Patent No.: US 10,549,387 B2
(45) Date of Patent: Feb. 4, 2020

(54) ENCLOSURE COVER

(71) Applicant: COVIDIEN LP, Mansfield, MA (US)

(72) Inventors: Curtis German, Longmont, CO (US);
Jeff D. Phillips, Loveland, CO (US);
Christopher C. Noe, Westminster, CO (US)

(73) Assignee: COVIDIEN LP, Mansfield, MA (US)

( * ) Notice: Subject to any disclaimer, the term of this patent is extended or adjusted under 35 U.S.C. 154(b) by 441 days.

(21) Appl. No.: 15/428,231

(22) Filed: Feb. 9, 2017

(65) Prior Publication Data

US 2018/0221992 A1 Aug. 9, 2018

(51) Int. Cl.
| | | |
|---|---|---|
| *B23K 26/12* | (2014.01) | |
| *B65D 43/02* | (2006.01) | |
| *B23K 26/70* | (2014.01) | |
| *A61B 17/00* | (2006.01) | |
| *B65D 43/14* | (2006.01) | |
| *B23K 26/21* | (2014.01) | |
| *B23K 101/20* | (2006.01) | |

(52) U.S. Cl.
CPC ............ *B23K 26/706* (2015.10); *A61B 17/00* (2013.01); *B23K 26/21* (2015.10); *B65D 43/14* (2013.01); *A61B 2017/00526* (2013.01); *B23K 2101/20* (2018.08)

(58) Field of Classification Search
CPC .............................. B23K 26/127; B65D 43/26
See application file for complete search history.

(56) References Cited

U.S. PATENT DOCUMENTS

| | | | | |
|---|---|---|---|---|
| 4,879,452 A * | 11/1989 | Kovarik | ................. | B23K 23/00 219/130.4 |
| 5,022,524 A * | 6/1991 | Grady | ....................... | B65D 5/22 206/395 |
| 5,086,923 A * | 2/1992 | King | .................... | B65D 25/107 206/308.1 |
| 5,464,963 A * | 11/1995 | Hostler | .............. | B23K 26/0823 219/121.6 |
| 5,519,184 A * | 5/1996 | Umlas | .................. | B23K 26/206 219/121.63 |
| 5,658,476 A * | 8/1997 | Gullo | .................. | B23K 26/0823 219/121.82 |
| 6,855,911 B1 * | 2/2005 | Lai | ......................... | B23K 26/03 219/121.86 |
| 2001/0054607 A1 * | 12/2001 | Pratt | ....................... | B23K 26/12 219/121.86 |
| 2005/0115941 A1 * | 6/2005 | Sukhman | ................ | B32B 15/08 219/121.86 |

(Continued)

*Primary Examiner* — Dana Ross
*Assistant Examiner* — Lawrence H Samuels
(74) *Attorney, Agent, or Firm* — Carter, DeLuca & Farrell LLP (57) ABSTRACT

A cover includes a base plate, an orbital disc, a plate slide and a disc slide. The cover is configured for positioning over an opening of a light-tight enclosure. The base plate includes an aperture, a bore and a slot defined therein. The base plate is configured to engage the enclosure. The orbital disc includes an aperture defined therein, a wall disposed adjacent the aperture, and a slot defined therein. The orbital disc is configured to at least partially engage the bore of the base plate. The plate slide is configured to slidingly engage the slot of the base plate. The disc slide is configured to slidingly engage the slot of the orbital disc.

10 Claims, 7 Drawing Sheets

(56) References Cited

U.S. PATENT DOCUMENTS

| | | | |
|---|---|---|---|
| 2005/0161446 A1* | 7/2005 | Fuson | B23K 15/0046 |
| | | | 219/121.82 |
| 2008/0017620 A1* | 1/2008 | Sukhman | B23K 26/12 |
| | | | 219/121.86 |
| 2009/0020513 A1* | 1/2009 | O'Halloran | B23K 26/12 |
| | | | 219/121.72 |
| 2013/0146568 A1* | 6/2013 | Moffitt | H01L 21/428 |
| | | | 219/121.61 |
| 2016/0144454 A1* | 5/2016 | Gabriel | B23K 26/127 |
| | | | 264/400 |

* cited by examiner

ENCLOSURE COVER

BACKGROUND

Technical Field

The present disclosure relates to a cover for enclosures, and, more particularly, to a light-tight cover for enclosures that allows for movement of an arm that passes through the cover.

Background of Related Art

When manufacturing and assembling surgical instruments, it is often desired to weld two or more components together. Further, a light-tight enclosure is commonly used to optimize the assembly process when using laser welds. For example, during assembly of jaw members of a surgical instrument, the jaw members may be placed within a light-tight enclosure, and a laser arm may be used to laser weld a pivot pin to a clevis. Here, the laser arm extends through a hole within the enclosure in a sealed manner. However, the tightly sealed fit between the laser arm and the boundaries of the hole in the enclosure restricts or limits the ability of the laser arm to move with respect to the enclosure.

During production or assembly of the product, it is often necessary to move the laser arm (e.g., an umbilical arm) to accommodate the new laser arm or robot movements. This typically involves disassembling the weld station or enclosure, removing the laser fiber (which is very delicate) and vision cables, removing the enclosure top panel, covering the existing opening, making a new opening, securing the new umbilical location and reinstalling the cables. This process is time consuming and can damage sensitive components.

The ability of the laser arm to be able to move with respect to the enclosure while still maintaining a light-tight seal is desirable to allow the laser arm to efficiently create laser welds on different portions of the instrument and/or on different instruments.

SUMMARY

The present disclosure relates to a cover configured for positioning over an opening of a light-tight enclosure. The cover includes a base plate, an orbital disc, a plate slide, and a disc slide. The base plate includes an aperture, a bore and a slot defined therein, and is configured to engage the enclosure. The orbital disc includes an aperture defined therein, a wall disposed adjacent the aperture, and a slot defined therein, and is configured to at least partially engage the bore of the base plate. The plate slide is configured to slidingly engage the slot of the base plate. The disc slide is configured to slidingly engage the slot of the orbital disc.

In aspects of the present disclosure, the plate slide includes a pair of wings. Each wing of the pair of wings is configured to engage a groove defined in the base plate adjacent the slot of the base plate to help prevent light from passing between the plate slide and the base plate.

In other aspects, the disc slide includes a pair of wings. Each wing of the pair of wings is configured to engage a groove defined in the orbital disc adjacent the slot of the orbital disc to help prevent light from passing between the disc slide and the orbital disc.

In still other aspects, the aperture of the base plate is approximately the same size as the opening of the enclosure.

In yet other aspects, the aperture of the orbital disc is smaller than the aperture of the base plate. In additional aspects, a diameter of the bore is at least one of the same size or larger than an outer diameter of the orbital disc.

In aspects of the present disclosure, the orbital disc is circular and the bore of the base plate is circular.

In still other aspects, the orbital disc is movable within the bore and with respect to the base plate when the base plate is engaged with the enclosure, and the base plate is fixed from movement with respect to the enclosure when the base plate is engaged with the enclosure.

In yet other aspects, engagement between the wall of the orbital disc and the base plate limits the movement of the orbital disc with respect to the base plate.

The present disclosure also relates to a method of manufacturing at least one component of an instrument. The method includes, positioning an instrument in a light-tight enclosure, utilizing a laser to produce a desired effect on the instrument where the laser enters the light-tight enclosure through an aperture of an orbital disc of an enclosure cover, and moving the orbital disc with respect to a base plate of the enclosure cover such that the laser is repositioned with respect to the instrument while the enclosure remains light-tight.

In aspects of the disclosure, the method further includes inserting a wire from the laser through a slot in the base plate, and through a slot in the orbital disc of the enclosure cover.

In other aspects, the method includes sliding a plate slide through the slot of the base plate after inserting the wire through the slot in the base plate.

In yet other aspects, the method includes sliding a disc slide through the slot of the orbital disc after inserting the wire through the slot in the orbital disc.

In still other aspects, the method includes utilizing the laser to produce a second desired effect on the instrument after moving the orbital disc with respect to the base plate of the enclosure cover.

In additional aspects, moving the orbital disc with respect to the base plate of the enclosure cover includes moving the orbital disc within a bore defined in the base plate.

BRIEF DESCRIPTION OF THE DRAWINGS

Various aspects of the present disclosure are described herein with reference to the drawings wherein like reference numerals identify similar or identical elements.

DETAILED DESCRIPTION

Embodiments of the presently disclosed enclosure cover are described in detail with reference to the drawings, in which like reference numerals designate identical or corresponding elements in each of the several views.

Figure 1:
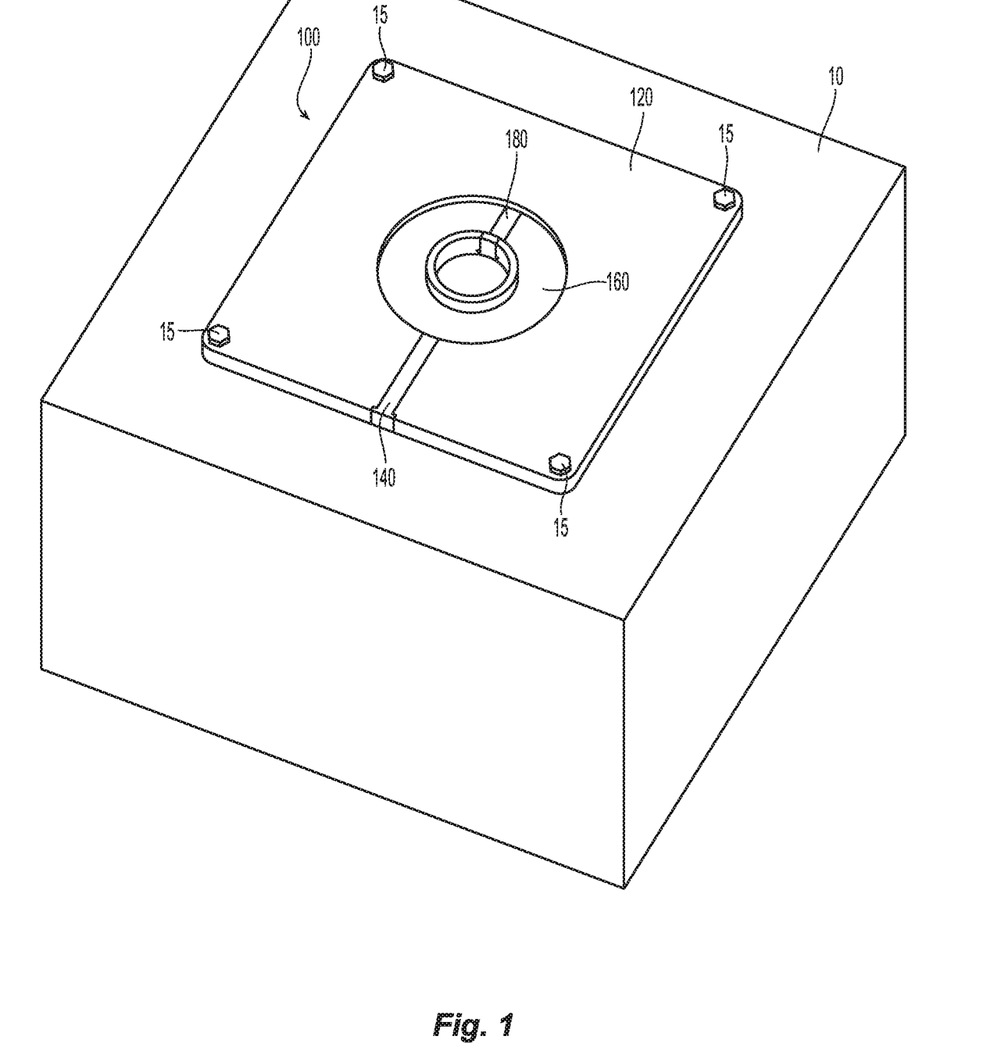
FIG. 1 is a perspective view of an enclosure including an enclosure cover in accordance with the present disclosure.

With initial reference to FIG. 1, an embodiment of an enclosure cover in accordance with the present disclosure is shown generally identified by reference character 100. Although enclosure cover 100 is shown configured for use in connection with the assembly and manufacture of surgical instruments, the present disclosure is equally applicable for utilizing the enclosure cover 100 for the assembly and/or manufacture of other devices where the use of a light-tight enclosure may be desired.

Figure 2:
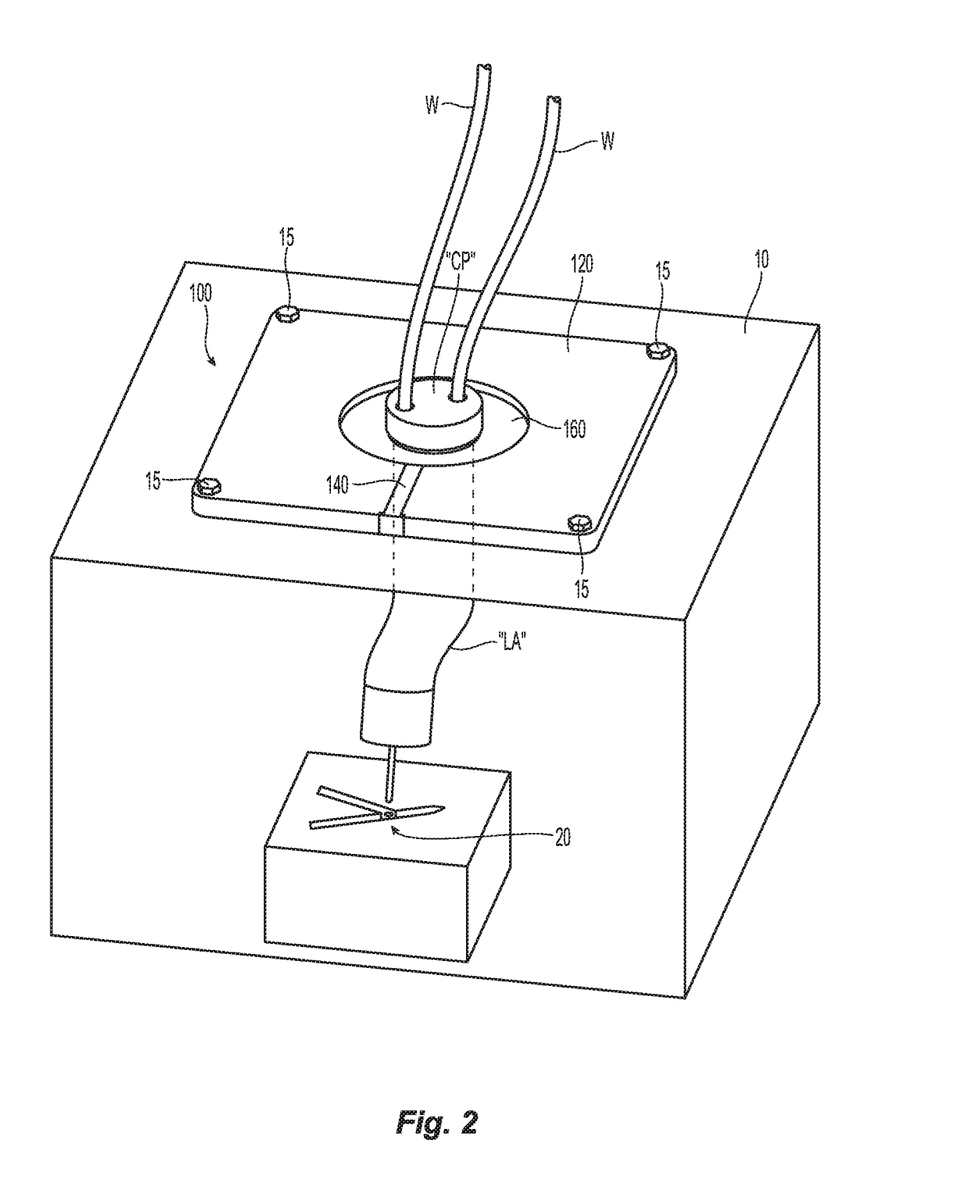
FIG. 2 is a perspective view of the enclosure and the enclosure cover of FIG. 1 illustrating a laser arm inserted through the enclosure cover.

With initial reference to FIGS. 1 and 2, enclosure cover 100 is configured for use with an enclosure 10 (e.g., a light-tight enclosure). Such a light-tight enclosure 10 is often suitable for the manufacture and assembly of various devices (e.g., a surgical instrument 20, or portions thereof). During many assembly and manufacturing methods, light entering or exiting enclosure 10 can negatively impact the quality of the process. For example, when laser welding is performed within enclosure 10, the escape of light from within enclosure 10 can result in a poor quality weld. Additionally, the escape of light from within enclosure 10 represents a hazard to personnel in the immediate area of enclosure 10.

Additionally, when laser welding while utilizing current light-tight enclosures for the manufacture and assembly of various instruments, the laser arm "LA" is typically positioned through a hole defined in the enclosure, and is sealed to prevent entry or exit of light. However, the positioning and sealing of the laser arm "LA" through the hole in the enclosure makes it difficult or impossible to move the laser arm "LA" (e.g., to weld different components or instruments), even slightly, while maintaining a light-tight enclosure and without unduly stressing various components of the laser arm "LA."

Enclosure cover 100 of the present disclosure allows for movement (e.g., lateral and rotational movement) of a laser arm "LA" (FIG. 2) passing therethrough, while maintaining a light-tight enclosure 10, thus providing greater flexibility and efficiency when assembling or manufacturing various instruments.

Figure 3:
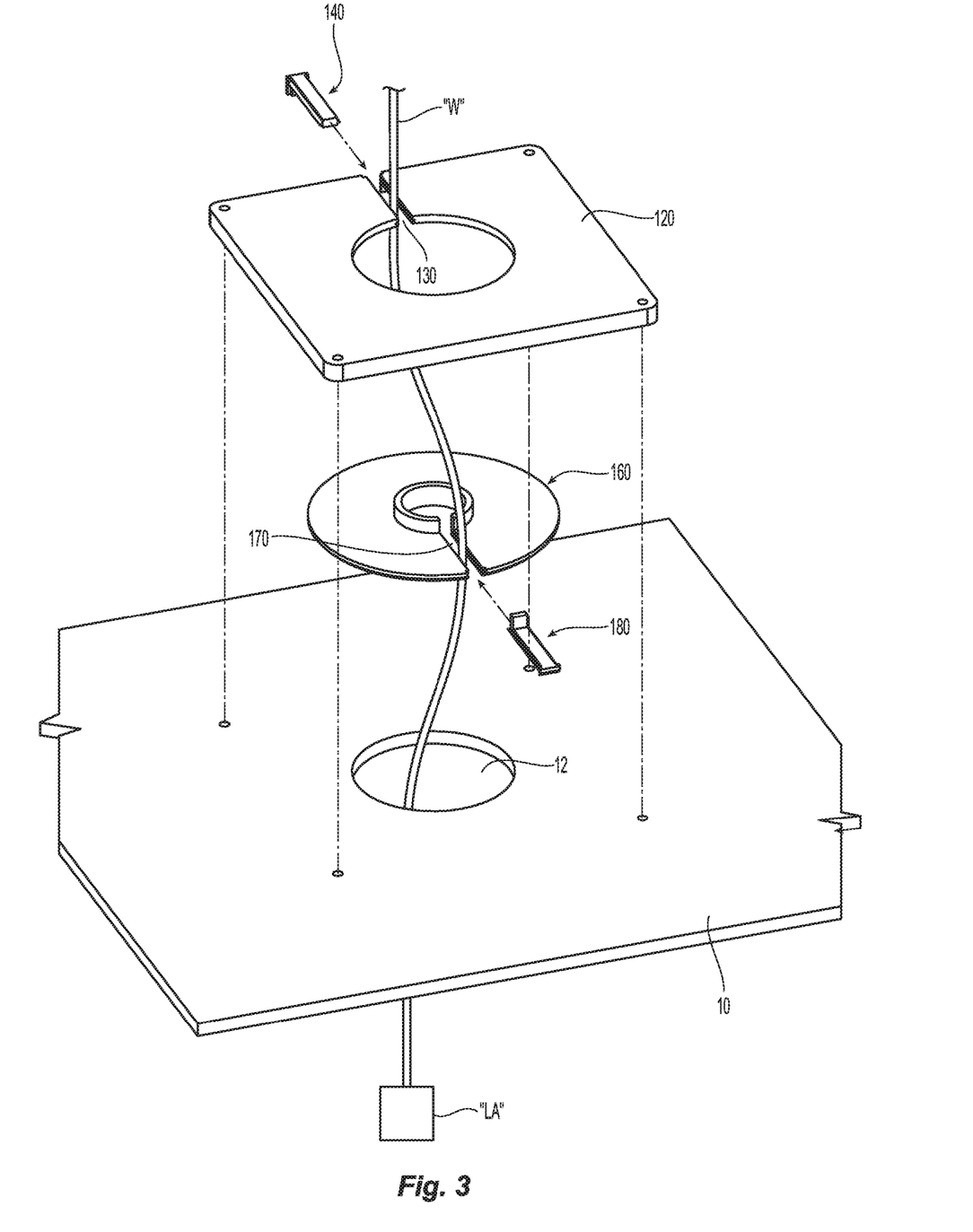
FIG. 3 is an assembly view of the enclosure cover of FIGS. 1 and 2.

With reference to FIG. 3, enclosure cover 100 includes a base plate 120, a plate slide 140, an orbital disc 160 and a disc slide 180. Generally, orbital disc 160 is positioned over a hole 12 defined within a wall of enclosure 10, orbital disc 160 is positioned within a bore 125 (FIGS. 5 and 7) defined within base plate 120, and base plate 120 is secured to enclosure 10. In this configuration, orbital disc 160 is positioned between base plate 120 and enclosure 10, and is movable with respect to base plate 120 and enclosure 10. As shown in FIG. 3, wires "W" or cables of the laser arm "LA" are threaded through a slot 130 defined within base plate 120, and through a slot 170 defined within orbital disc 160 such that the wire(s) "W" can communicate with the laser arm "LA" within enclosure 10 and with a portion of a welding tool which is outside of enclosure 10.

Further, to preserve the light-tight integrity of enclosure cover 100, plate slide 140 is slidable within slot 130 of base plate 120 to occlude the passage of light through slot 130, and disc slide 180 is slidable within slot 170 of orbital disc 160 to occlude the passage of light through slot 170.

Figure 4:
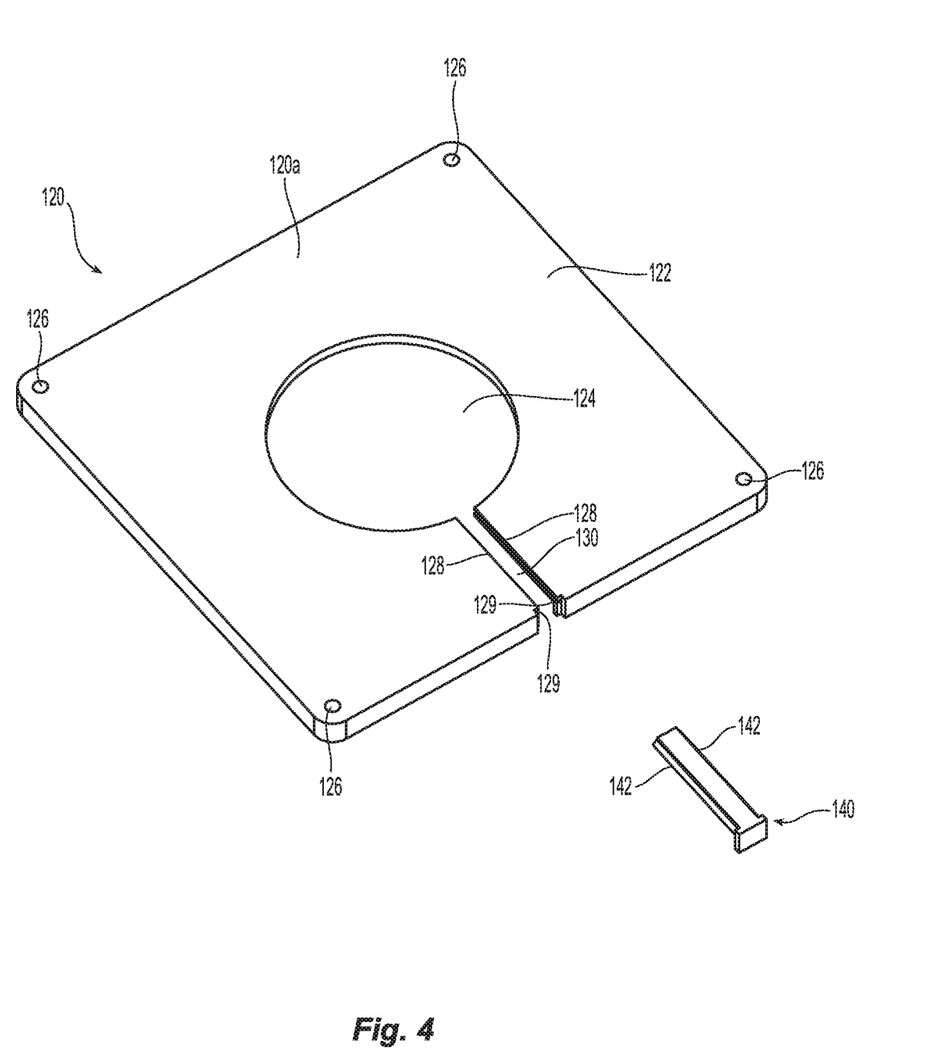
FIG. 4 is a perspective view of a base plate and a plate slide of the enclosure cover of FIGS. 1-3.

With particular reference to FIG. 4, base plate 120 and plate slide 140 are shown. Base plate 120 includes a body portion 122, a central aperture 124 defined therein, and slot 130 defined in body portion 122 extending between an edge of body portion 122 and central aperture 124. Base plate 120 also includes four openings 126 defined generally in the corners of body portion 122. Each opening 126 is configured to allow a fastener 15 (FIGS. 1 and 2) to pass therethrough to facilitate the securement between base plate 120 and a wall of enclosure 10.

Central aperture 124 of base plate 120 is configured for placement adjacent (e.g., directly over) hole 12 of enclosure 10 (FIG. 3), and may be sized similarly or exactly the same (i.e., diameter) as hole 12. Slot 130 of base plate 120 extends between central aperture 124 and an edge of body portion 122. Slot 130 is configured to allow at least one wire "W" to be positioned from an area external to base plate 120, through central aperture 124. Slot 130 is bound by a pair of walls 128 of body portion 122 of base plate 120. Each wall 128 includes a groove or channel 129 therein, which is configured to slidingly engage a wing 142 of plate slide 140. The engagement between wings 142 of plate slide 140 and grooves 129 within walls 128 of body portion 122 helps prevent light from being able to pass between an upper surface 120a of base plate 120 and a lower surface 120b (FIG. 5) of base plate 120, thereby restricting light from being able to enter or exit enclosure 10 through slot 130.

Figure 5:
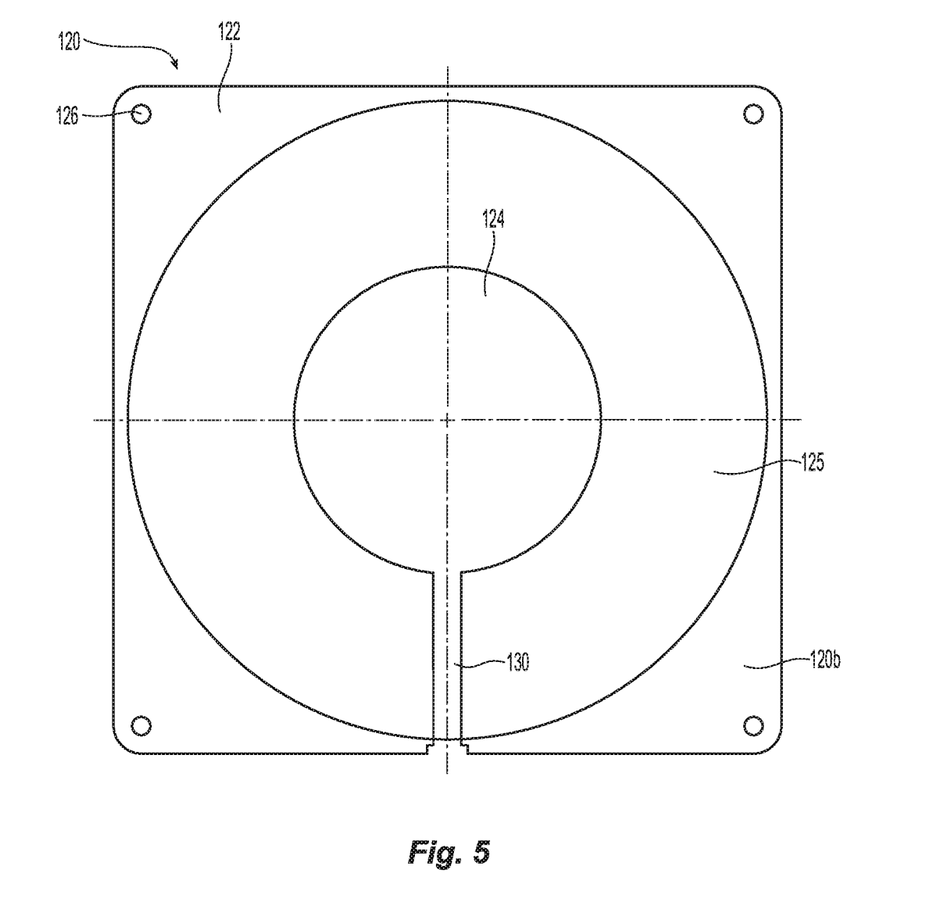
FIG. 5 is a plan view of the bottom of the base plate of FIG. 4.
Figure 7:
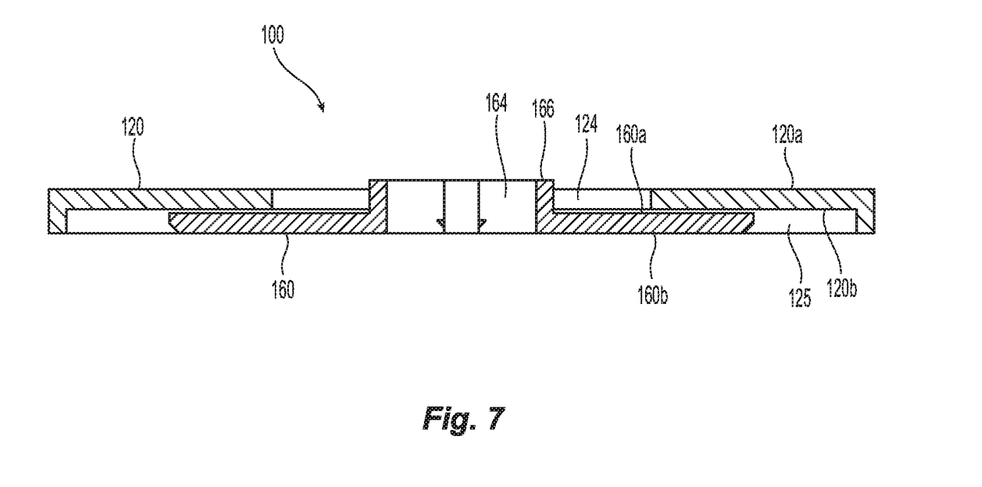
FIG. 7 is a side view of the base plate of FIGS. 4 and 5 engaged with the orbital disc of FIG. 6.

Referring now to FIGS. 5 and 7, base plate 120 includes a bore 125 within its lower surface 120b. When base plate 120 is engaged with enclosure 10, bore 125 is configured to help retain orbital disc 160 therein. Bore 125 is circular in shape, and is larger in diameter than orbital disc 160 such that orbital disc 160 can move in any direction along the top of enclosure 10 with respect to base plate 120.

Figure 6:
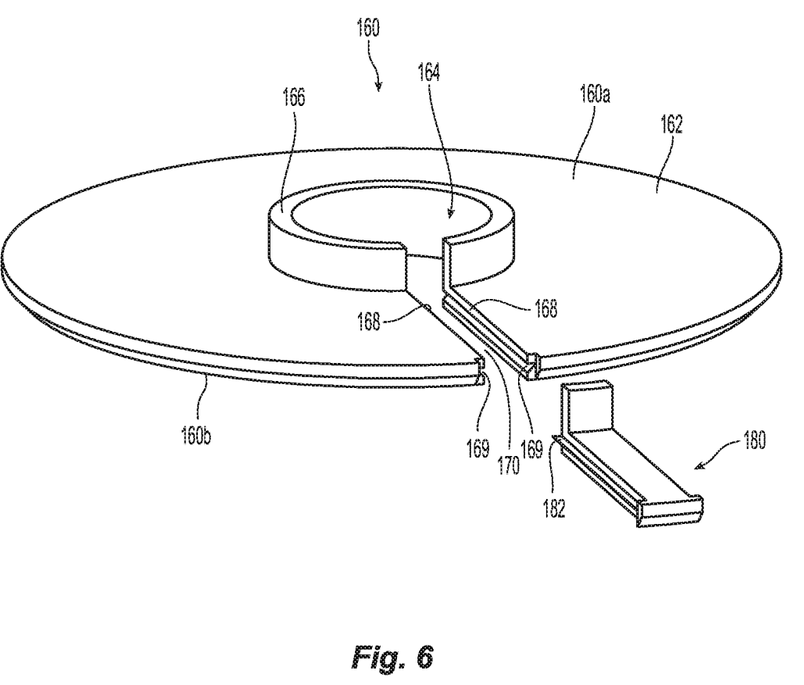
FIG. 6 is a perspective view of an orbital disc and a disk slide of the enclosure cover of FIGS. 1-3.

With reference to FIG. 6, orbital disc 160 and disc slide 180 are shown. Orbital disc 160 includes a body portion 162, a central aperture 164 defined therein, and slot 170 defined in body portion 162 extending between an edge of body portion 162 and central aperture 164. Orbital disc 160 also includes a circular wall 166 disposed adjacent central aperture 164 and which defines central aperture 164. Circular wall 166 is taller than or extends from body portion 162.

Orbital disc 160 is adapted to be positioned between base plate 120 and enclosure 10 (e.g., within bore 125 of base plate 120), such that circular wall 166 of orbital disc 160 extends through central aperture 124 of base plate 120 (see FIG. 7). Additionally, orbital disc 160 is able to move in any direction within a plane defined by body portion 162 of orbital disc 160 with respect to base plate 120 and with respect to enclosure 10. Engagement between circular wall 166 and the walls defining central aperture 124 of base plate 120 limits the movement of orbital disc 160 with respect to base plate 120 and enclosure 10.

As shown in FIG. 7, central aperture 164 of orbital disc 160 includes a smaller diameter than central aperture 124 of base plate 120. Additionally, as shown in FIG. 2, central aperture 164 of orbital disc 160 is similarly sized to a connecting portion "CP" of laser arm "LA" such that, when engaged, light cannot pass between the connecting portion "CP" of laser arm "LA" and circular wall 166.

Central aperture 164 of orbital disc 160 is configured for placement between (e.g., sandwiched between) hole 12 of enclosure 10 (FIG. 3) and central aperture 124 of base plate 120. Slot 170 of base plate orbital disc 160 extends between central aperture 164 and an edge of body portion 162. Slot 170 is configured to allow at least one wire "W" to be positioned from an area external to orbital disc 160, through central aperture 164. Slot 170 is bound by a pair of walls 168 of body portion 162 of orbital disc 160. Each wall 168 includes a groove or channel 169 therein, which is configured to slidingly engage wings 182 of disc slide 180. The engagement between wings 182 of disc slide 180 and grooves 169 within walls 168 of body portion 162 helps prevent light from being able to pass between an upper surface 160a of orbital disc 160 and a lower surface 160b of orbital disc 160, thereby restricting light from entering or exiting enclosure 10 through slot 170.

Further, while the present disclosure describes a particular type of engagement between slides 140, 180 and respective slots 130, 170 (e.g., utilizing wings and grooves) to help enable a light-tight engagement therebetween, other types of engagement between slides 140, 180 and slots 130, 170 which also produce a light-tight connection are also contemplated.

Accordingly, enclosure cover 100 of the present disclosure enables a laser arm "LA" to move with respect to enclosure 10 (e.g., with respect to the location where the laser arm "LA" enters the enclosure 10) while maintaining a light-tight enclosure 10.

Additionally, enclosure cover 100 allows a second device to be removed and/or inserted into enclosure 10 without compromising the light-tight benefits of enclosure 10. For example, if a second device was within enclosure 10 and needed to be removed (e.g., for calibration or replacement), enclosure cover 100 can be removed from enclosure 10 to allow the second device to be removed from enclosure 10 through as within enclosure 10 and needed to be removed (e.g., for calibration or replacement), enclosure cover 100 can be removed from enclosure 10 to allow the second device to be removed from enclosure 10 through hole 12 of enclosure 10. A cable connected to the second device can be removed or disengaged from enclosure cover 100 through slots 130 and 170.

The present disclosure also relates to positioning and repositioning a laser arm "LA" with respect to an enclosure 10 while maintaining the light-tight characteristics of the enclosure 10, as described above. When repositioning the laser, the portion of the laser arm "LA" that passes through aperture 164 of orbital disc 160 remains fixed from movement with respect to orbital disc 160 while orbital disc 160 moves with respect to base plate 120. Further, the present disclosure relates to methods of manufacturing instruments utilizing the disclosed enclosure 10 and enclosure cover 100.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A cover configured for positioning over an opening of a light-tight enclosure, the cover comprising
   a base plate including an aperture, a bore and a slot defined therein, the base plate configured to engage the enclosure;
   an orbital disc including an aperture defined therein, a wall disposed adjacent the aperture, and a slot formed therein, the orbital disc configured to at least partially engage the bore of the base plate;
   a plate slide configured to slidingly engage the slot of the base plate; and
   a disc slide configured to slidingly engage the slot of the orbital disc.

2. The cover according to claim 1, wherein the plate slide includes a pair of wings, each wing of the pair of wings configured to engage a groove defined in the base plate adjacent the slot of the base plate to help prevent light from passing between the plate slide and the base plate.

3. The cover according to claim 1, wherein the disc slide includes a pair of wings, each wing of the pair of wings configured to engage a groove defined in the orbital disc adjacent the slot of the orbital disc to help prevent light from passing between the disc slide and the orbital disc.

4. The cover according to claim 1, wherein the aperture of the base plate is approximately the same size as the opening of the enclosure.

5. The cover according to claim 1, wherein the aperture of the orbital disc is smaller than the aperture of the base plate.

6. The cover according to claim 5, wherein a diameter of the bore is at least one of the same size or larger than an outer diameter of the orbital disc.

7. The cover according to claim 1, wherein the orbital disc is circular.

8. The cover according to claim 1, wherein the bore of the base plate is circular.

9. The cover according to claim 1, wherein the orbital disc is movable within the bore and with respect to the base plate when the base plate is engaged with the enclosure, and wherein the base plate is fixed from movement with respect to the enclosure when the base plate is engaged with the enclosure.

10. The cover according to claim 9, wherein engagement between the wall of the orbital disc and the base plate limits the movement of the orbital disc with respect to the base plate.

* * * * *